(12) United States Patent
Rushing

(10) Patent No.: US 6,567,171 B1
(45) Date of Patent: May 20, 2003

(54) DIGITAL DENSITOMETER WITH CONTROLLED LIGHT EMITTER

(76) Inventor: Allen J. Rushing, 429 Tara La., Webster, NY (US) 14580

( * ) Notice: Subject to any disclaimer, the term of this patent is extended or adjusted under 35 U.S.C. 154(b) by 0 days.

(21) Appl. No.: 09/542,260

(22) Filed: Apr. 3, 2000

(51) Int. Cl.[7] .......................... G01N 21/49; G03G 15/00
(52) U.S. Cl. ...................................... 356/432; 355/208
(58) Field of Search ................................ 356/432, 425; 355/208

(56) References Cited

U.S. PATENT DOCUMENTS

| | | | |
|---|---|---|---|
| 3,830,401 A | 8/1974 | Benwood et al. | |
| 4,068,956 A | 1/1978 | Taboada | |
| 4,397,932 A | 8/1983 | Young | |
| 4,473,029 A | 9/1984 | Fritz et al. | |
| 4,546,060 A | 10/1985 | Miskinis et al. | |
| 4,553,033 A | 11/1985 | Hubble, III et al. | |
| 5,117,119 A | 5/1992 | Schubert et al. | |
| 5,119,132 A | 6/1992 | Butler | |
| 5,173,750 A | 12/1992 | Laukaitis | |
| 5,649,266 A | 7/1997 | Rushing | |
| 5,900,960 A | 5/1999 | Reime | |
| 6,385,411 B1 | 5/2002 | Anthony et al. | |

OTHER PUBLICATIONS

Daniel Cognard, William Nunley, "Thermal Behavior of GaAs LEDs," Application Bulletin 200, Jul. 1989, Optek Technology, Inc., Carrollton, TX, USA.

J. W. Davidson, III, Lowell Johnson, Application Bulletin 206, Jul. 1989, Optek Technology, Inc, Carrollton, TX, USA.

Kirk Bailey, "Understanding Infrared Diode Power Ratings," Application Bulletin 207, Jul. 1989, Optek Technology, Inc., Carrollton, TX, USA.

Jim Woods, "Optimizing Power Output Using the OP232W," Application Bulletin 215, May 1993, Optek Technology, Inc., Carrollton, TX, USA.

Martin McCrorey, Application Bulletin 210, Jul. 1989, Optek Technology, Inc., Carrollton, TX, USA.

"Infrared Emitters and Phototransistors," Optoelectronics Data Book, 1998, EG&G Vactec, St. Louis, MO, USA.

T. E. Eichenberger, "Designing a 'Wide–Gap Optical Switch' using an OP293/OP298 (plastic TO–46 equivalent) LED and OP593/OP598 (plastic TO–18 equivalent) phototransistor," Application Bulletin 209, Jan., 1985, Optek Technology, Inc., Carrollton, TX, USA.

*Primary Examiner*—Hung Xuan Dang
*Assistant Examiner*—Mohammad Abutayeh

(57) ABSTRACT

A densitometer with a controllable light emitter intensity operates to reduce excessive exposure of sensitive materials, such as photoconductive film. During normal printer operation, the emitter is operated in a pulsed-mode, thereby reducing emitter temperature and prolonging its useful life. Exposure of the photoconductor is also reduced, which may prolong its useful life and avoid image defects. The pulse width, frequency, and duty-cycle are chosen to give these benefits without compromising density measurement capability. The emitter drive circuitry is connected to a motion sensor so that emitter intensity is reduced to a low level when photoconductor motion is stopped. A test mode is provided during which the emitter intensity is reduced by a calibrated amount, simulating the presence of a calibrated test sample.

20 Claims, 6 Drawing Sheets

DIGITAL DENSITOMETER WITH CONTROLLED LIGHT EMITTER

FIELD OF THE INVENTION

This invention relates generally to densitometers for measuring optical density. In particular, the invention relates to optical density measurement of toner-covered test patches or other areas for controlling process parameters in electrostatographic apparatus such as copiers and printers.

BACKGROUND OF THE INVENTION

In electrostatographic apparatus such as copiers and printers, automatic adjustment of process control parameters is used to produce images having well regulated darkness or optical density. Copier and printer process control strategies typically involve measuring the transmissive or reflective optical density of a toner image on an exposed and developed area (called a "test patch") of an image receiver. Optical density has the advantage, compared to transmittance or reflectance measures, of matching more closely to human visual perception. A further advantage, especially for transmission density, is that density is approximately proportional to the thickness of the marking material layer, over a substantial range.

Typically, toned process control test patches are formed on the photoconductor in interframe regions of the photoconductor, i.e., between image frame areas. An "onboard" densitometer measures the test patch density, either on the photoconductor or after transfer of the patches to another support member. From these measurements, the machine microprocessor can determine adjustments to the known operating process control parameters such as primary charger setpoint, exposure setpoint, toner concentration, and development bias.

A transmission type of densitometer is particularly well suited to transmissive supports. In this type, a light source projects light, visible or infrared, through an object onto a photodetector such as a photodiode. In a copier/printer, the photoconductor passes between the light source and the photodetector. When the photoconductor has toner on the surface, the amount of light reaching the photodetector is decreased, causing the output of the densitometer to change. Based on this output, the amount of toner applied to the photoconductor can be varied as required in order to obtain consistent image quality. Another type of densitometer as described in U.S. Pat. No. 4,553,033 to Hubble, III et al uses reflected light flux rather than transmitted light flux to determine density, and is particularly suited to opaque reflective supports.

Whether of the transmissive or reflective type, the densitometer photodetector signal is input to signal processing circuitry, either analog or digital. The modem trend is toward digital circuitry, such as disclosed in U.S. Pat. No. 5,117,119 to Schubert et al. The Schubert et al densitometer is auto-ranging, where one of several available ranges is utilized according to the density of the test sample. The individual ranges span a factor of 10 in transmittance or reflectance, equivalent to 1.0 density units.

Photoconductors tend to be fatigued, i.e., degraded in their photoconductive characteristics for subsequent imaging cycles, after long or repeated exposure to light, resulting in degraded image quality. Improvements in photoconductor formulation, disclosed for example in U.S. Pat. No. 4,397,932 to Young, have been helpful in reducing the fatigue problem, but fatigue remains an issue for many photoconductors in use today. For this reason, copiers and printers are typically designed to minimize the exposure of the photoconductive member to unwanted non-imaging light, such as room light. Light-tight machine enclosures, careful service procedures, and careful photoconductor belt or drum packaging and installation are typically used to minimize the room light exposure. However, light sources within the machine enclosure remain a potential cause of photoconductor fatigue.

In some instances, light sources within the machine enclosure can be shielded from the photoconductor. This can be effective with electro-optical devices commonly used to sense the position and motion of image receiver sheets, for example.

In many copier/printer configurations, an on-board densitometer employs a light source directed at a spot on the photoconductor, for the aforementioned purpose of process control. Shielding would defeat the function and purpose of the densitometer. After prolonged exposure of the photoconductor by the densitometer light emitter, fatigue and image defects can result. The severity of the problem depends on the spectral sensitivity of the photoconductor and the spectral emission of the densitometer light source, as well as the intensity and duration of the exposure.

In some applications the spectral sensitivity of the photoconductor does not match the spectral emission of the densitometer light source. For example, a visible red-sensitive photoconductor may not be significantly affected by the emissions of a densitometer having an infrared light-emitting diode (LED) light source. In that case the emitter may be left fully energized indefinitely, even when the photoconductor is motionless between print jobs, without causing image defects. Continuous operation in this manner is not only convenient, but also avoids warm-up effects except when first turned on.

However, many preferred photoconductors have spectral sensitivity extending through the visible range into the near infrared. In these cases the infrared light emitted from the densitometer and incident on the photoconductor can cause significant fatigue, leading to defective images. The problem is most acute in any spot on the photoconductor that is parked motionless opposite the energized densitometer light emitter when the machine is idle between jobs.

Another problem with on-board densitometers is that their typical LED's or other emitter types do not have the ideal constant light intensity for density measurement. Short-term instability results from temperature sensitivity during warm-up. In continuous-mode operation at a fairly high LED current, unstable warm-up periods of a minute or more are commonly observed. Additional longer-term instability results from gradual degradation of the LED with age. Complicated and expensive approaches may be required to avoid inaccurate measurements due to these instabilities. Such approaches include extended warm-up periods, temperature compensation, intensity feedback control, and periodic recalibration.

Operating an LED in a pulsed-mode is a well-known approach to reducing average power dissipation and reducing PN junction temperature rise. When a current pulse is applied, the typical LED PN junction temperature response includes a component with a fast time constant of about 10 to 40 milliseconds. Pulsed-mode operation with a pulse-width much less than this, say a few hundred microseconds or less, along with a low duty-cycle, minimizes temperature rise, improves light emission stability during warm-up, and prolongs LED useful life.

In densitometer applications, pulsed-mode operation has been used to isolate a density signal from an ambient light or noise signal, as in U.S. Pat. No. 5,173,750 to Laukaitis, and U.S. Pat. No. 5,900,960 to Reime. Benwood et al (U.S. Pat. No. 3,830,401) use pulsed-mode LED operation to monitor the reflectivity of a developer mixture of relatively reflective carrier particles and light-absorbing toner particles. Butler (U.S. Pat. No. 5,119,132) discloses a pulsed-mode reflection densitometer suitable for both black and colored toner over a wide density range. Pulsed-mode operation has also been used to enable higher intensity for measurement of higher-density samples, as in U.S. Pat. No. 4,068,956 to Taboada. For densitometry of toner images on a photoconductor, pulsed-mode operation obviously reduces the exposure of the photoconductor, compared to continuous operation at the same intensity. The reduced exposure of pulsed-mode operation can be beneficial in reducing the aforementioned problem of photoconductor fatigue.

In the case of a moving photoconductor, a problem with pulsed-mode densitometer operation is that too low a pulse frequency can yield measurements too widely separated on the test sample. On the other hand, too high a pulse frequency results in greatly overlapping measurement spots on the photoconductor. With a fixed minimum pulse width required for measurement acquisition, a pulse frequency too high, with a high duty-cycle, sacrifices much of the exposure reduction advantage of pulsed-mode operation. With the greatly overlapped measurement spots, there is little compensating advantage gained in measurement continuity.

Another difficulty with densitometer pulsed-mode operation is that the photodetector output is valid only when the LED is energized, and these times might not match the times when density readings are needed on the moving photoconductor. That is, the density readings might not be taken at the spots where readings are needed, such as on process control patches. Another potential problem is that the time when the LED is pulsed might not match the time when the host processor or LCU reads the densitometer output.

While pulsed-mode operation reduces exposure, it does not totally eliminate the problem of fatiguing the photoconductor in spots parked motionless opposite a pulsing LED. Time periods of minutes or even hours between jobs are quite common, even in high volume production environments. Depending on the photoconductor formulation, even a low duty-cycle pulsed-mode exposure of such duration could severely fatigue any spot parked opposite the pulsing LED. This could result in persistent image defects in subsequent jobs, or require costly replacement of the photoconductor.

Another problem with on-board densitometers is related to initial setup and service. For test, calibration, and diagnostic purposes, a service technician will typically carry one or more calibrated density test standards for insertion into the on-board densitometer. The densitometer output is then monitored to verify densitometer function and accuracy. Gaining access to the densitometer for these tests is inconvenient, requiring the opening of machine covers and, in many cases, removal of machine parts. Moreover, the tests cannot be performed if the test standards are unavailable.

SUMMARY OF THE INVENTION

One object of the present densitometer invention is to stabilize LED intensity and prolong the LED useful life by operating in a pulsed-mode. Average power and temperature of the LED is greatly reduced. This permits operation at higher intensities for brief pulses, enabling density measurements of higher-density test samples. The lower temperature rise results in more stable light output, and prolongs the useful life of the LED. The pulse frequency is selected according to the effective measurement spot size and photoconductor velocity, so as not to degrade densitometer data collection capability in a copier/printer application. Further stabilization of LED intensity is obtained by monitoring a signal representing the densitometer emitter output and feeding back to adjust the emitter drive circuit. The emitter drive circuit adjusts LED current in a manner to regulate the LED light output.

Another object of the present invention is to hold the density output signal steady between LED pulses. This prevents invalid density readings from being presented, either to a human-readable display or to a host processor.

Another object of the present invention is to reduce photoconductor fatigue caused by exposure from the densitometer light emitter. The densitometer pulse duty-cycle is kept low, so that total exposure of the photoconductor is greatly reduced, compared to continuous mode operation. Again, the pulse frequency is selected according to measurement spot size and photoconductor velocity, so as not to degrade densitometer data collection capability in a copier/printer application.

Still another object of the present invention to prolong LED useful life and reduce photoconductor fatigue by automatic reduction of exposure from the LED between jobs. The LED drive circuit is connected to a photoconductor motion status sensor, such as an encoder. If the sensor indicates no motion, an interval timer begins and times out if the photoconductor remains motionless longer than the timer setting. When the timer times out, the LED is switched to a low intensity or off, or the pulse duty-cycle is reduced substantially below the normal duty-cycle value.

Full intensity and normal duty-cycle are restored when motion resumes. If the normal pulse duty-cycle is low enough, the low temperature rise largely eliminates the warm-up problem that occurs with continuous mode operation. An override may be provided to restore normal duty-cycle and intensity while the photoconductor is motionless, permitting density measurement of a motionless photoconductor.

It is yet another object of the present invention to provide a functional test and calibration of the densitometer. On a command signal, the densitometer LED drive circuit reduces the LED intensity by a calibrated amount, simulating the insertion of a calibrated test standard. There is no need for the service technician to carry calibrated test standards and no need to gain physical access to the densitometer. Time required for densitometer test and calibration is reduced, and there is no risk of lost, forgotten, smudged, or damaged calibration standards.

To obtain these objects, a densitometer with a controllable light emitter intensity is disclosed. During normal printer operation, the emitter may be operated in a pulsed-mode, thereby reducing emitter temperature and prolonging its useful life. Exposure of the photoconductor is also reduced, which may prolong its useful life and avoid image defects. The pulse width, frequency, and duty-cycle are chosen to give these benefits without compromising density measurement capability.

Whether in pulsed or continuous operation, the emitter drive circuitry is connected through a timer to a motion status sensor so that exposure from the emitter is reduced below the normal level when the photoconductor motion is stopped. A test mode is provided during which the emitter intensity is reduced by a calibrated amount, simulating the presence of a calibrated test standard. An emitter stabilization circuit regulates the emitter light output, even when there is no room to position a sensor to monitor the output of the emitter shining on the photoconductor.

BRIEF DESCRIPTION OF THE DRAWINGS

The subsequent description of the preferred embodiments of the present invention refers to the attached drawings wherein.

DETAILED DESCRIPTION OF THE PREFERRED EMBODIMENTS

I. Electrophotographic Printing Machine Environment

Because apparatus of the general type described herein are well known the present description will be directed in particular to elements forming part of, or cooperating more directly with, the present invention. While the invention will be described with reference to imaging apparatus and particularly to an electrophotographic system, the invention can also be used in other imaging apparatus and in environments not in the imaging field.

Figure 1:
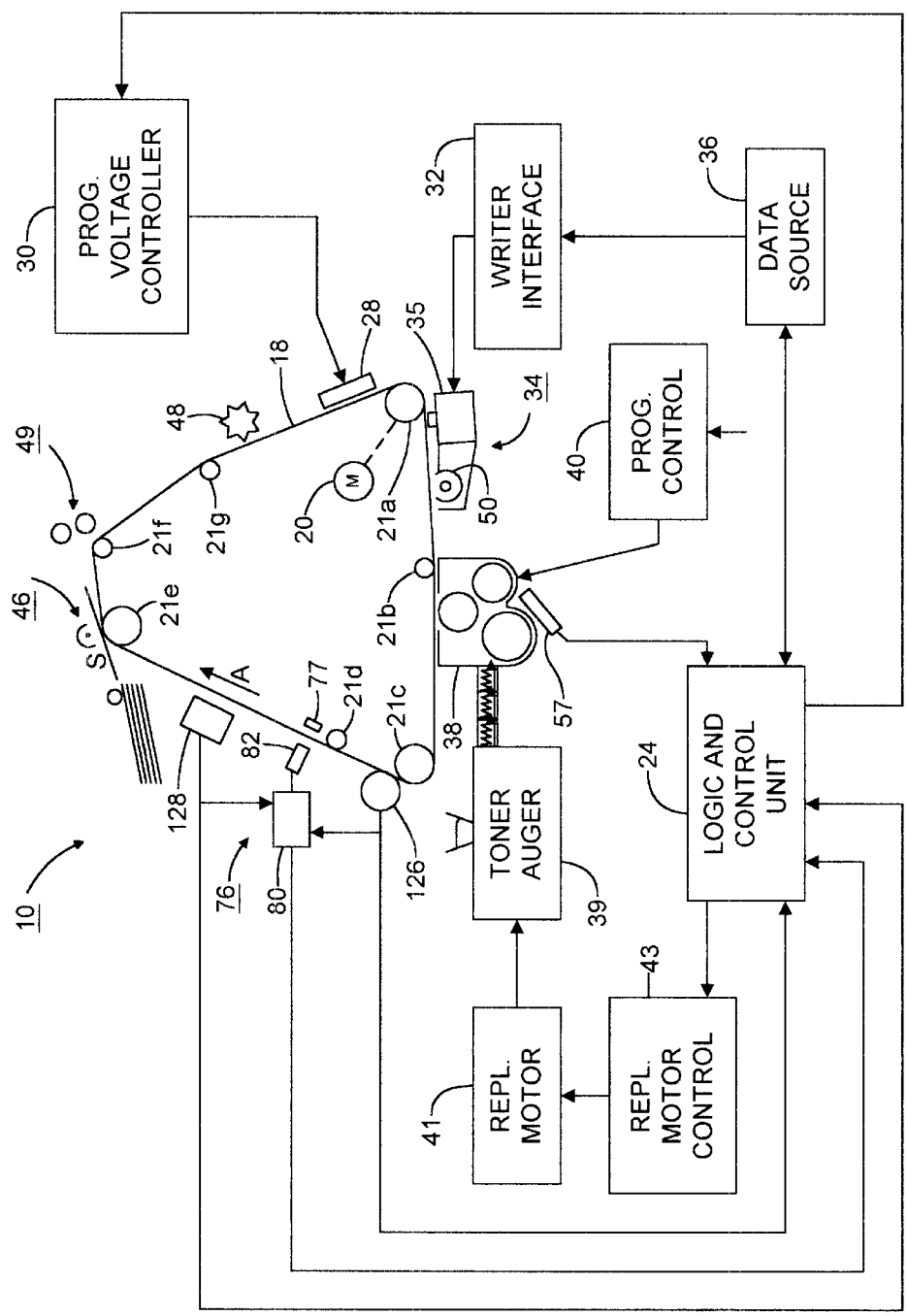
FIG. 1 is a side elevational view in schematic form of an electrophotographic apparatus to illustrate one environment for the use of this invention.

With reference to the electrophotographic copier and/or printer machine 10 as shown in FIG. 1, a moving recording member such as photoconductive belt 18 is entrained about a plurality of rollers or other supports 21a–21g one or more of which are driven by a motor 20 so as to advance the belt in a direction indicated by an arrow "A" past a series of workstations of machine 10. A logic and control unit 24, which has a digital computer, has a stored program for sequentially actuating the workstations in response to signals from various sensors and encoders, as is well known.

A primary charging station 28 sensitizes belt 18 by applying a uniform electrostatic charge of predetermined primary voltage $V_0$ to the surface of the belt. The output of the charging station is regulated by a programmable voltage controller 30, which is in turn controlled by logic and control unit 24 to adjust primary voltage $V_0$ for example through control of electrical potential ($V_{grid}$) to a grid that controls movement of corona charges from charging wires to the surface of the recording member, as is well known. Other known forms of chargers, including roller chargers, may also be used.

At an exposure station 34, projected light from a write head 35 dissipates the electrostatic charge on the photoconductive belt to form a latent image of a document to be copied or printed. The write head preferably has an array of light-emitting diodes or other light source such as a laser or other spatial light modulator for exposing the photoconductive belt picture element (pixel) by picture element with a regulated intensity and exposure, $E_0$. Alternatively, the exposure may be by optical projection of an image of a document or a patch onto the photoconductor.

Where a light-emitting diode or other electro-optical exposure source or writer is used, image data for recording is provided by a data source 36 for generating electrical image signals. The data source 36 may be a computer, a document scanner, a memory, a data network, etc. Signals from the data source and/or logic and control unit may also provide control signals to a writer interface 32 for identifying exposure correction parameters in, for example, a LUT for use in controlling image density. Travel of belt 18 brings the areas bearing the latent charge images into a development station 38. The development station has one (more if color) magnetic brushes in juxtaposition to, but spaced from, the travel path of the belt. Magnetic brush development stations are well known. For example, see U.S. Pat. No. 4,473,029 to Fritz et al and U.S Pat. No. 4,546,060 to Miskinis et al. Other types of development stations may be used as is well known and plural development stations may be provided for developing images in plural colors or with toners of different physical characteristics.

Logic and control unit 24 selectively activates the development station in relation to the passage of the image areas containing latent images to selectively bring the magnetic brush into engagement with or a small spacing from the belt. The charged toner particles of the engaged magnetic brush are attracted imagewise to the latent image pattern to develop the pattern.

Conductive portions of the development station, such as conductive applicator cylinders, act as electrodes. The electrodes are connected to a variable supply of D.C. potential $V_B$ regulated by a programmable controller 40. Details regarding the development station are provided as an example, but are not essential to the invention.

A transfer station 46 as is also well known is provided for moving a receiver sheet "S" into engagement with the photoconductive belt in register with the image for transferring the image to a receiver. Alternatively, an intermediate member may have the image transferred to it and the image may then be transferred to the receiver. A cleaning station 48 is also provided subsequent to the transfer station for removing toner from the belt 18 to allow reuse of the surface for forming additional images. In lieu of a belt, a drum photoconductor or other structure for supporting an image may be used. After transfer of the unfixed toner images to a receiver sheet, such sheet is detacked from the belt and transported to a fuser station 49 where the image is fixed.

The logic and control unit provides overall control of the apparatus and its various subsystems as is well known. Programming commercially available microprocessors is a conventional skill well understood in the art.

Figure 2:
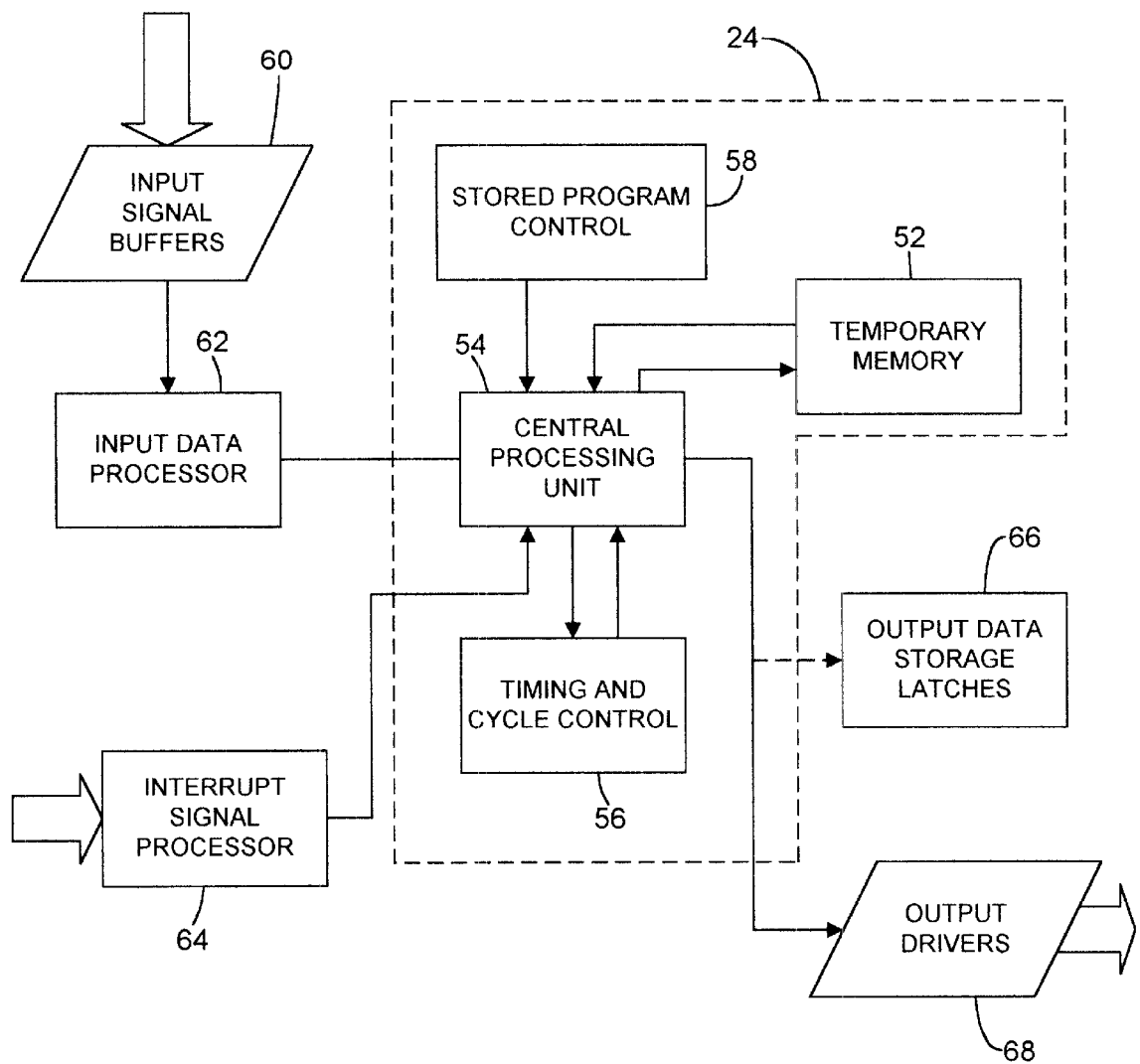
FIG. 2 is a block diagram of a logic and control unit for controlling the apparatus of FIG. 1.

Referring to FIG. 2, a block diagram of a typical logic and control unit 24 is shown. The logic and control unit comprises temporary data storage memory 52, central processing unit 54, timing and cycle control unit 56, and stored program control 58. Data input and output is performed sequentially through or under program control. Input data are applied either through input signal buffers 60 to an input data processor 62 or through an interrupt signal processor 64. The input signals are derived from various switches, sensors, and the analog-to-digital (A/D) converters that are part of the apparatus 10 or received from sources external to machine 10.

The output data and control signals are applied directly or through storage latches 66 to suitable output drivers 68. The output drivers are connected to appropriate subsystems.

Process control strategies generally utilize sensors to provide real-time control of the electrostatographic process and to provide "constant" image quality output from the user's perspective.

Referring again to FIG. 1, one such sensor for process control may be a densitometer 76 to monitor development of test patches in non-image areas of photoconductive belt 18, as is well known in the art. See for example U.S. Pat. No. 5,649,266 to Rushing. The densitometer measurements are needed to insure that the transmission or reflection density of toned areas on the belt is maintained. The densitometer may include a visible or infrared LED 77 which shines light through the belt or reflected by the belt onto a photodiode detector 82, which is connected to a densitometer circuit 80. The photodiode detector may be separate from the densitometer circuit, as shown in FIG. 1, or may be on the same circuit board as the densitometer circuit components.

For a transmission densitometer, LED 77 may be on the untoned side of belt 18 and detector 82 on the toned side, as shown. Alternatively, the reverse arrangement is also workable. For a reflection densitometer, the emitter and detector would both be on the toned side of the belt. The photodiode detector generates an electrical signal that varies directly with the flux of light received. The densitometer circuit converts the detector signal to a density value.

A rotary encoder 126 engaging belt 18 outputs logic pulses corresponding to the motion of the belt. The pulse output enables the densitometer 76 to collect density readings synchronously with the belt motion. The pulse output is also connected to LCU 24 for the purpose of synchronizing the operation of the various workstations. A "SYNC" pulse motion sensor 128 outputs a SYNC pulse, preferably only one for each belt once-around, to provide an indication of the absolute position of belt 18.

In the case of transmission density, the total, or gross, measured density value is reduced by the stored density value of the bare untoned patch, to obtain a value $D_{NET}$, representative of the net toner density. The net signal is also representative of the thickness of the toner deposit averaged over the measured area, and also representative of the toner mass per unit area. The $D_{NET}$ signal may be used to adjust process parameters $V_0$, $E_0$, or $V_B$.

The $D_{NET}$ signal may also be used to assist in the maintenance of the proper concentration of toner particles in the developer mixture by having the logic and control unit provide control signals to a replenisher motor control 43. Replenisher motor control 43 controls replenisher motor 41 that in turn drives a toner auger 39 for feeding new toner particles into development station 38. A toner concentration monitor probe 57 provides signals to the logic and control unit about relative concentration of toner particles to carrier particles in the developer mix.

Another sensor useful for monitoring process parameters is an electrometer probe 50 which is mounted at a location preferably downstream of corona charging station 28, relative to the direction of the movement of belt 18. In FIG. 1 electrometer probe 50 is mounted immediately downstream of writehead 35.

II. First Preferred Densitometer Embodiment (Unsynchronized)

Figure 3:
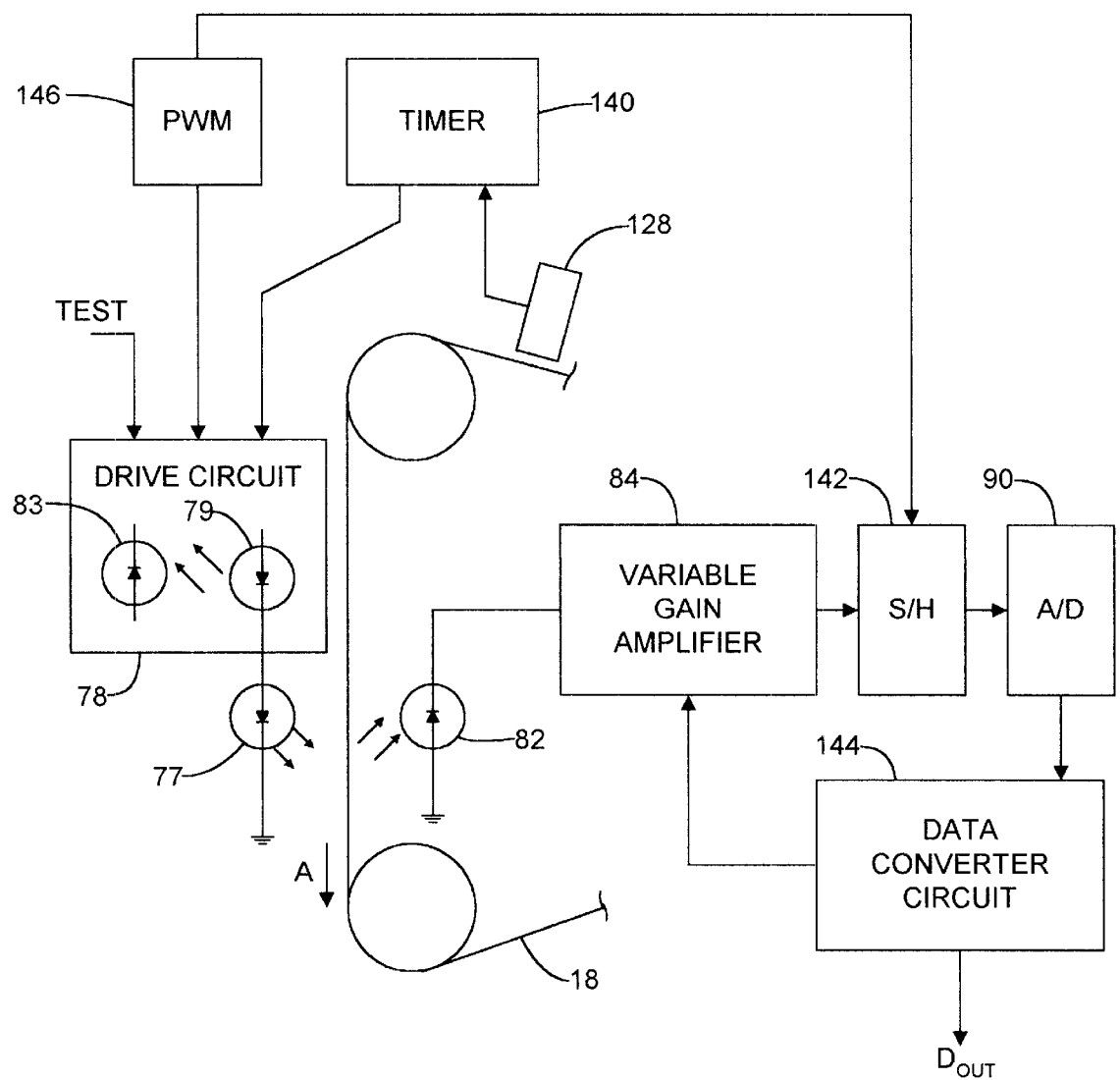
FIG. 3 is a block diagram of a densitometer according to a first preferred embodiment of the present invention, unsynchronized.

The structure and operation of a first preferred densitometer embodiment may be understood with reference to the block diagram of FIG. 3. The separate functional blocks shown in FIG. 3, such as a timer 140, a variable gain amplifier 84, a sample-and-hold (S/H) circuit 142, an A/D converter 90, and a data converter 144, may be physically separate circuits or devices. Alternatively, some of them may be incorporated within the same device, such as a microcontroller ($\mu$C). Image supporting structure 18, moveable in the direction indicated by arrow "A", may be in the form of a web or belt, a portion of which is shown in FIG. 3, or in the form of a rotating drum. SYNC pulse motion sensor 128 produces a signal indicating whether the supporting structure is in motion.

The preferred motion sensor 128 senses regularly spaced reference marks or perforations on the web. The reference marks on the web or drum may be of any form detectable by a sensor, such as optical, mechanical, or magnetic sensors. The reference mark detector senses the passage of reference marks on the moving web or drum, and produces a pulse whenever a reference mark is detected. The reference mark detector thus produces a pulse signal while the belt is in motion, with a frequency proportional to the web velocity.

In the case of an image supporting structure in the form of an endless belt or drum, only a single reference mark is needed, which passes the detector repeatedly while the endless web or drum advances. If multiple reference marks are used, they are preferably equally spaced around the loop or drum circumference. The detector senses the reference marks, producing a SYNC pulse signal each time a reference mark passes the sensor, which is synchronous with the motion of the loop or drum.

Alternatively, a rotary encoder can be used for motion sensing, without need for reference marks. In that case the motion of the web drives the encoder, and the encoder generates SYNC pulses with a frequency proportional to the web velocity. The encoder may be coupled through one of the rollers, or may engage the web directly. Still other methods for generating a web or drum motion signal may be envisioned. The motion signal need not indicate the velocity of motion, but only the motion status. The motion signal may indicate whether there is motion at any velocity or no motion; only a binary (motion/no motion) signal is required.

Yet another motion sensing alternative is an indirect or inferred motion signal, obtained by evaluating the density measurements, without need for motion sensing hardware. When the web or drum is in motion, normal nonuniformity in marking material coverage across the image areas causes the density measurements to vary greatly. Even a perfectly uniform density on the web or drum will not yield a perfectly unvarying density measurement, owing to various noise sources associated with the motion. A belt seam will typically provide density nonuniformity in the region of the seam, sufficient for inferring motion as the seam passes the densitometer. However, when the web or drum is stopped, the repeated density measurements at a single spot become substantially unvarying.

Density variation can be numerically characterized and calculated in terms of, for example, standard deviation or range (maximum minus minimum). The range calculation simply requires saving the maximum and minimum measurements collected over a defined period of time or a defined number of measurements, and then subtracting the minimum from the maximum. A range less than a predetermined threshold, over a defined time period, indicates that motion has stopped. The range measurements and calculations can be periodically updated, to indicate when motion resumes.

In some cases, reliability of the inferred motion signal may be improved by using hysteresis, with two threshold values for variability. Variability exceeding the higher threshold would trigger a reliable "motion resumed" indication, while variability less than the lower threshold would trigger a reliable "motion stopped" indication. Variability between the two thresholds, where motion may or may not be present, would not trigger possibly false or unreliable indications of changed motion status. A microcontroller, such as Microchip Corporation model PIC16C715, within the densitometer circuit can be programmed to compute density variation in terms of range or in other variation terms, and produce an inferred motion signal.

Returning to FIG. 3, the motion signal in this embodiment is produced by SYNC sensor 128. The SYNC sensor and the densitometer are shown in separate positions, with the SYNC sensor upstream relative to the densitometer. The positions shown in FIG. 3 are illustrative only, and do not rule out other positions in other embodiments. A space-saving configuration could have both sensors located at substantially the same position. For example, the SYNC sensor could be located on the same circuit board as the densitometer circuit.

The aforementioned SYNC signal is connected to the timer, which may be within a microcontroller. The pulses of the SYNC signal repeatedly reset the timer while the web is in motion, preventing the timer from timing out. If web motion stops, SYNC pulses cease, the timer times out, and an LED drive circuit 78 stops pulsing LED 77, leaving it in the deenergized state. The LED remains deenergized until the timer circuit again receives SYNC pulses. An override command may be provided to energize the LED even when the web is stopped, to obtain a density measurement of the stationary web.

With continuing reference to FIG. 3, a pulse-width modulation (PWM) circuit 146 controls the LED pulse-width and frequency. To substantially reduce the light exposure on the web, the pulse-width and frequency is set such that the duty-cycle is small, say, less than 50%. The PWM circuit output is also connected to the S/H circuit. The sampling instant of the S/H circuit is delayed slightly after the LED pulse begins, to allow for photodiode 82 and amplifier 84 response times. The S/H circuit output to A/D converter 90 is held steady between LED pulses, to avoid an invalid response.

An alternative for holding the density signal steady between LED pulses, instead of the S/H circuit shown in FIG. 3, is an A/D converter with an integral sample-and-hold capability. The PWM circuit output is used to generate an A/D latching signal synchronous with the LED pulses.

A/D converter 90 output is input to data converter circuit 144. The data converter circuit sets the gain of amplifier 84 and generates the scaled density value, $D_{OUT}$. The data converter typically contains a lookup table (LUT), whereby the $D_{OUT}$ value corresponding to the amplifier gain setting and the A/D converter output is obtained. Another alternative to the S/H circuit, for holding the density signal steady between LED pulses, is to latch the LUT output synchronously with the LED pulses.

The scaled density value, $D_{OUT}$, is output, according to the application, to a display, a data storage device, a host processor, or other output device.

The measurement spot size limits the fidelity with which the densitometer output tracks high-spatial frequency density patterns on the web, especially sharp edges. Small measurement spot size is required to spatially resolve individual lines in high-frequency parallel line patterns.

The measurement spot corresponds to that area of the web that blocks, by absorption, reflection, or scattering, light flux from the emitter that would otherwise impinge upon the photodiode. Depending on the geometry of the emitter-web-photodiode configuration and the light emission pattern, the illuminated area of the web may be larger than this effective measurement spot size. Also, the photodiode sensitive area may be larger or smaller than the effective measurement spot.

The effective measurement spot diameter can be approximately determined by testing with apertures of various diameters in thin opaque sheets. Alternatively, an iris diaphragm having a continuously variable aperture may be used. With the web preferably removed, the aperture is placed in the plane of the web, aligned between emitter and photodiode for maximum photodiode signal. Beginning with a very small aperture, the photodiode signal increases with incident light flux as the aperture is increased. A threshold aperture diameter is determined beyond which there is no significant change in the signal.

Typically, owing to emitter beam divergence and imperfect beam intensity uniformity, there will not be a perfectly abrupt threshold aperture diameter in the foregoing procedure. Therefore an approximation may be made. An aperture diameter producing a photodiode signal of, say, 50% of the signal produced by a very large diameter, approximately defines an effective measurement spot size. The result will typically be dependent on the distance between the emitter and the aperture, and possibly between aperture and photodiode. Therefore the test would preferably be done with the same spacing as during normal operation, with the aperture in the plane of the web.

Another approach to determining effective measurement spot size, not dependent on precise alignment, is based on spatial frequency response. In this method, test samples having patterns of optically dense parallel lines, with spacing equal to the line width, are scanned in the transverse direction by the densitometer. As the line pattern spatial frequency increases, the peak-to-peak response of the photodiode diminishes. The cut-off frequency, at which the response is down from the low-frequency response by, say, 50%, approximately defines the effective measurement spot size. The effective measurement spot diameter is approximately equal to the line width at the cut-off frequency. For non-circular spots, this procedure characterizes the spot dimension in the process or scan direction.

The time required for the web to move a distance, d, is d/v, where v is the web velocity. When the LED is pulsed with a pulse-to-pulse period of d/v, measurement spots have a pitch length or center-to-center spacing of d on the web. If the effective measurement spot diameter is also d, the density measurement spots are just touching but not overlapped. A substantially faster pulse rate would obtain density measurements of greatly overlapping spots, highly correlated, with little new information, one to the next. The photoconductor would be subjected to unneeded exposure. Furthermore, an unnecessarily high pulse frequency requires faster hardware and software to process measurements from each pulse, and could result in needless expense. On the other hand, a substantially slower pulse rate would obtain density measurements at widely separated spots, leaving large gaps on the web with no density measurement.

For auto-ranging densitometers utilizing a sample-and-hold function from one spot reading to the next, selection of an appropriate pulse frequency is further complicated. When density on the web changes from one measurement spot to the next, the densitometer may reach the end of the range currently in use, and require a range change to obtain a valid measurement. After the range change, the next sampled spot is checked to determine if it is within the new range. A valid density measurement is not obtained until the range has been set to accommodate the new spot being measured. This can result in "skipped spots" of one or more spots, until the appropriate range is set.

A density change big enough to require two or three steps in range change will result in two or three successive "skipped spots", respectively. Successive "skipped spots" occur when there are large abrupt density changes to be measured, as at the edges of maximum density (Dmax) test patches, for example. For a density span of only 0.5 density units in each individual range (a span in each range of 1.0 density units is more typical), a change of density of at least 1.50 can be accommodated by a 3-step range change. In electrophotography, Dmax test patches having net transmission density exceeding 1.50 would be unusual, even for black toner.

Measurement continuity can be retained by setting the pulse frequency high enough to provide some spot overlap. With 50% overlap of diameters, any single "skipped spot" will not spoil measurement continuity. With 67% overlap, any two successive "skipped spots" will not spoil measurement continuity. With 75% overlap, any three successive "skipped spots" will not spoil measurement continuity. A pulse frequency of 2, 3, or 4 times v/d provides 50%, 67%, or 75% spot diameter overlap, respectively.

By analysis of the foregoing cases, a reasonable compromise between conflicting goals of minimum exposure and maximum measurement information is a pulse frequency between 2v/d and 4v/d, depending on the likelihood of "skipped spots". However, the maximum "skipped spot" sequence length could be zero for small sample density variation within a single densitometer range, or up to 4 successive "skipped spots" for large sample density variation and relatively small densitometer individual ranges. Accordingly, a pulse frequency providing measurement continuity without unnecessary exposure is generally between 1.0 and 5.0 times v/d. The pulse width is set for the minimum time necessary for measurement acquisition.

By way of example in calculating a preferred pulse frequency, consider electrophotographic Dmax toned test patches having net transmission density up to 1.45 density units. In this example, the auto-ranging densitometer has individual density ranges each spanning 0.50 density units, such that up to 3 "skipped spots" may occur during the transitions across the test patch edges. The measurement spot diameter is approximately 2 mm. The velocity of the test patches is 600 mm per second. The approximate preferred pulse frequency is then 4*600/2=1200 Hz. At this frequency, continuous density measurements are obtained from edge-to-edge across the patch itself and into the surrounding area. The patch edge effects, important in some evaluations, would be well-defined, within the limitations of the measurement spot size.

With reference again to FIG. 3, the "test" command input to LED drive circuit 78 simulates the insertion of a calibrated test sample in the optical path. The LED drive circuit responds to the "test" command by reducing the intensity of densitometer LED 77 by a precisely controlled factor. The LED may be driven either continuously or in a pulsed mode.

For example, suppose the "test" mode is designed to reduce emitted light intensity by a factor of precisely 4.00. Photodiode 82 responds as if a calibrated test standard with density of $\log_{10}(4.00)=0.60$ were inserted in the optical path. Likewise, data converter circuit 144 outputs a $D_{OUT}$ result as if a calibration standard of density 0.60 had been inserted. The test mode thus confirms the function and accuracy of the densitometer, with no need to physically insert a calibration standard.

One possible source for the "test" command is a tiny manual switch mounted on the densitometer circuit board and easily accessible by service personnel. One switch position causes drive circuit 78 to output the normal current to LED 77. The other position causes the drive circuit to output the reduced "test" current. Another possible source for the "test" command would be from an operator interface on the outside of the machine enclosure. In this case, there is no need to open the machine enclosure or disassemble parts to gain access to the densitometer.

A simple method for obtaining a somewhat coarse intensity control for the "test" command is to switch, within LED drive circuit 78, from a first current source to a second current source, where the second is set nominally to output a predetermined fraction of the first current level. A more precise method indicated in FIG. 3 uses an emitter feedback stabilization circuit within the emitter drive circuit, to compensate for intensity changes of LED 77 caused by temperature sensitivity and aging. These effects are substantial even when LED current is held constant. The emitter stabilization circuit is therefore beneficial even when there is no "test" command.

In operation, the emitter stabilization circuit adjusts the current through LED 77 to regulate its light output to a setpoint light intensity. The "test" command switches the setpoint from the normal value to a reduced value. The logarithm of the ratio of the normal setpoint divided by the reduced value is the simulated "test" density. During the LED warm-up period, and for up to a few minutes after switching setpoint, the LED current is automatically adjusted as required to compensate the temperature sensitivity of the LED light output efficiency. On a longer time scale, the emitter stabilization circuit adjusts the LED current to compensate for LED light output degradation with age.

As shown in FIG. 3, the densitometer LED 77, belt 18, and photodiode 82 are positioned close to each other. It is often impractical to mount a second photodiode to monitor the output of LED 77 without interfering with the aforementioned items or with the light beam. In the preferred embodiment shown in FIG. 3, a "tracking" LED 79, identical to LED 77, is mounted at a non-interfering nearby position, within LED drive circuit 78, and light-shielded from belt 18. The two identical LED's 77 and 79 are connected in series, so that they always operate with the same current. The two LED's are mounted equivalently with respect to heat dissipation, and in positions with equal ambient temperatures.

The two LED's will therefore experience substantially the same temperature cycles, current flow, and usage. Being of identical type, the two LED's will respond similarly to the aforementioned factors, and will track each other closely in light output, over changing ambient temperature, warm-up response, and long-term degradation with age. Some unit-to-unit variability is to be expected even for LED's of the same type, but with well-controlled manufacturing processes, this variability is small compared to the average effects of temperature, current, and age. Data published for the Optek LED type OP298, for example, indicate an average light output degradation of 14% after 50,000 hours of operation at 50 mA, compared to a unit-to-unit standard deviation of 1.8%.

A second photodiode 83 within LED drive circuit 78 monitors the light output from "tracking" LED 79. The emitter stabilization circuit responds by automatically adjusting the current through the two series-connected LED's. The circuit is designed using well-known principles of feedback control and circuit design to regulate the light output of "tracking" LED 79 to a setpoint value. Because the two identical series-connected LED's simultaneously experience the same current, temperature, and degradation with age, the light output of LED 77 shining through the belt will be substantially as well regulated as that of "tracking" LED 79 shining on photodiode 83 in the emitter drive circuit.

III. Second Preferred Densitometer Embodiment (Synchronized)

Figure 4:
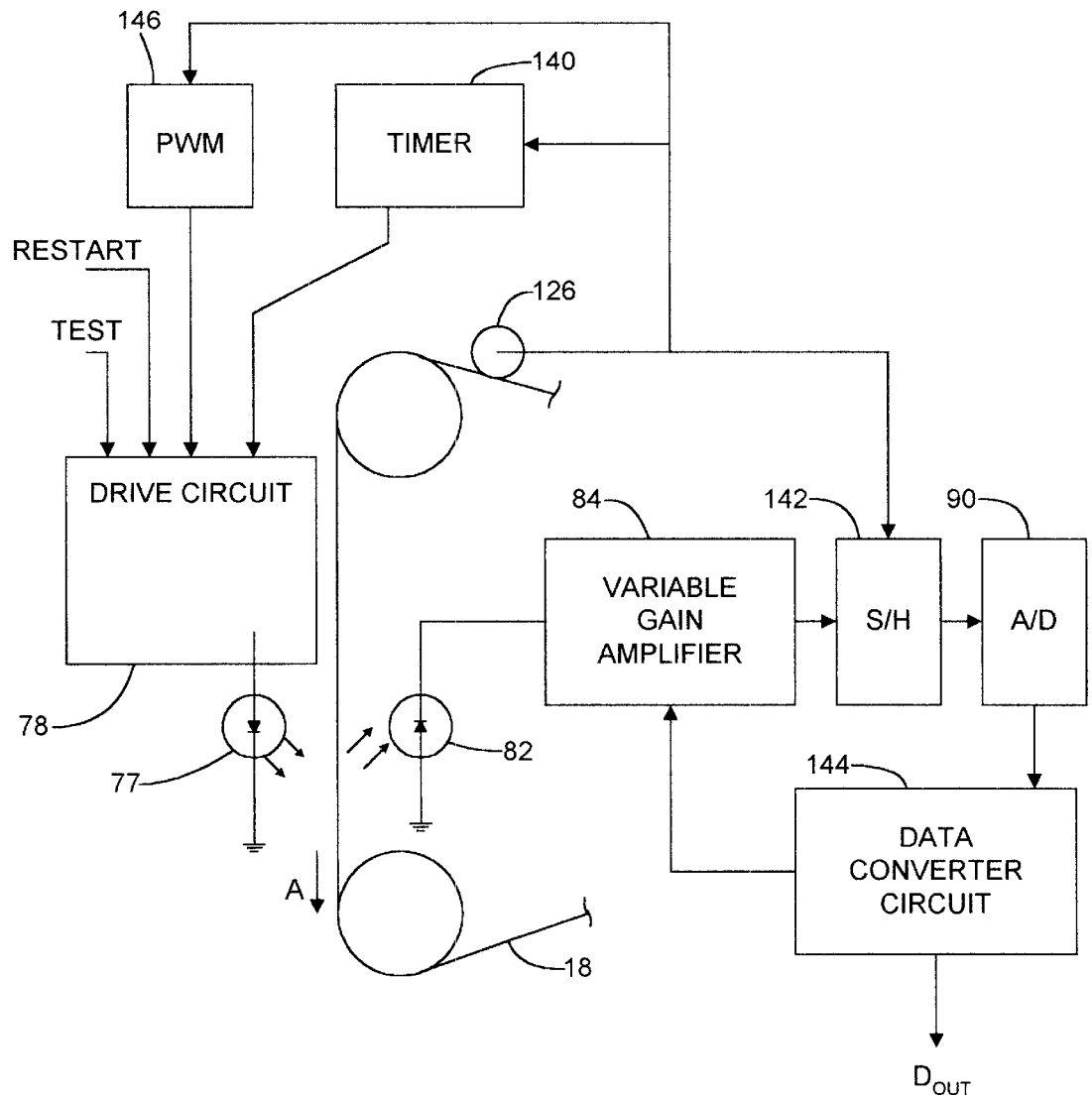
FIG. 4 is a block diagram of a densitometer according to a second preferred embodiment of the present invention, synchronized.

The structure and operation of the second preferred densitometer embodiment may be understood with reference to the block diagram of FIG. 4. As in the first preferred embodiment, some of the functional blocks, such as timer 140, variable gain amplifier 84, S/H circuit 142, A/D converter 90, and data converter circuit 144, may or may not be physically separate devices or circuits. Image supporting structure 18, moveable in the direction indicated by arrow "A", may be in the form of a web or belt, a portion of which is shown in FIG. 4, or in the form of a rotating drum. Rotary encoder 126 produces a "PERF" pulse signal synchronous with the motion of the belt. In the preferred embodiment of FIG. 4, rotary encoder 126 is coupled to the belt through perforations on the web engaging the teeth of a gear wheel on the shaft of the encoder. The encoder pulse signal is therefore referred to as the "PERF" signal, even though the encoder pulse frequency may be different from the actual perforation frequency. Alternatively to the rotary encoder, any type of encoder outputting a signal synchronous with the belt motion could also be used. The PERF pulses from rotary encoder 126 are output at times marking the movement of defined positions on the belt past a fixed point.

Rotary encoder 126 is coupled to the belt, either directly as shown, or through one of the rollers, so that the PERF pulse frequency is proportional to the belt velocity. The PERF pulses are output to PWM circuit 146, which controls the pulse frequency of LED 77 through drive circuit 78. The pulse frequency of LED 77 is thus adjusted proportional to any change in the PERF signal frequency, and any change in belt velocity.

Rotary encoder 126 and densitometer photodiode 82 are shown in FIG. 4 in separate positions. This is illustrative only, and does not preclude embodiments having both sensors located at substantially the same position. For example, the PERF sensor could be located on the same circuit board as the densitometer photodiode.

The PERF signal is also connected to S/H circuit 142. The PERF signal synchronizes the LED pulse and the sampling of the photodiode amplifier output. The S/H circuit output is held steady between LED pulses, at a level characteristic of the test sample density. Invalid density readings between LED pulses are thus avoided. Moreover, since the PERF signal is synchronous with the belt motion, the density sampling is at a defined spacing on the belt in the direction of motion.

The PERF signal is also connected to timer 140. The pulses of the PERF signal repeatedly reset the timer while the belt is in motion, preventing the timer from timing out. If web motion stops, PERF pulses cease, the timer times out, causing the LED drive circuit reduce the exposure from the LED. The LED continues in a low-exposure mode until the timer circuit again receives PERF pulses, or a "restart" signal is received.

Figure 5A:
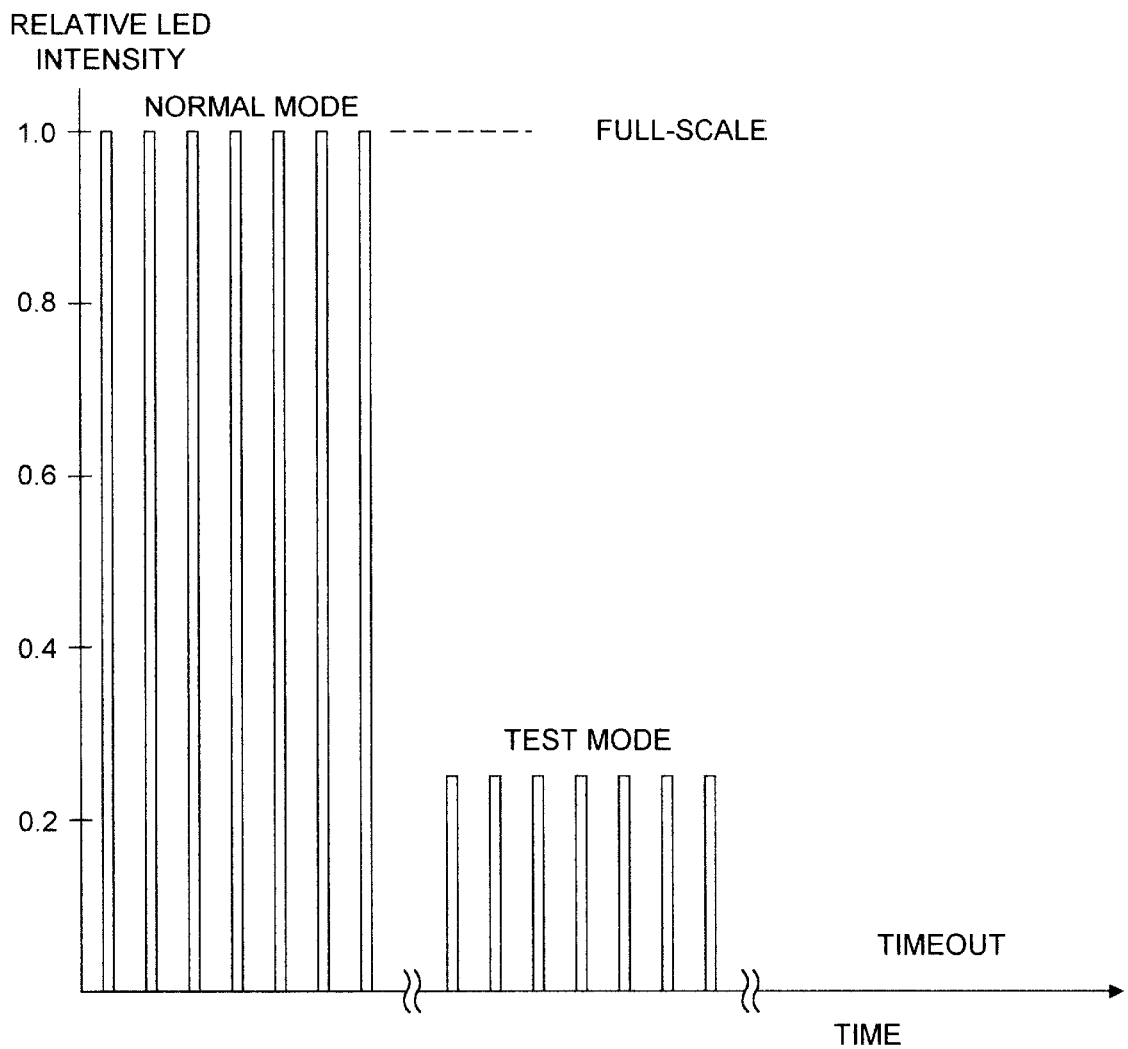
FIG. 5a is a graph of the emitter pulse intensity versus time for normal operation, test mode, and emitter turned off after timeout.

A graph of emitter pulse intensity versus time is shown in FIG. 5a, illustrating three modes of operation. Shown first on the time axis is normal mode operation, then test mode operation, and finally timeout. The pulse amplitude changes according to the mode, while the duty-cycle remains at about 20%. The test mode amplitude is ¼ of normal full amplitude, simulating the presence of a test sample with a density of log(¼)=0.60. After timeout, FIG. 5a shows the LED turned completely off. Alternatively, the timeout mode can switch to a low but non-zero pulse intensity. The timeout intensity level can be set low enough that the motionless photoconductor is not severely fatigued at the exposed spot, but high enough that density measurements can be obtained at least over a reduced density range, to detect when motion resumes. The foregoing values are illustrative only; other values may be used according to the application. While FIG. 5a shows different intensity levels during pulsed operation, continuous operation could also utilize modes of different intensity levels.

Figure 5B:
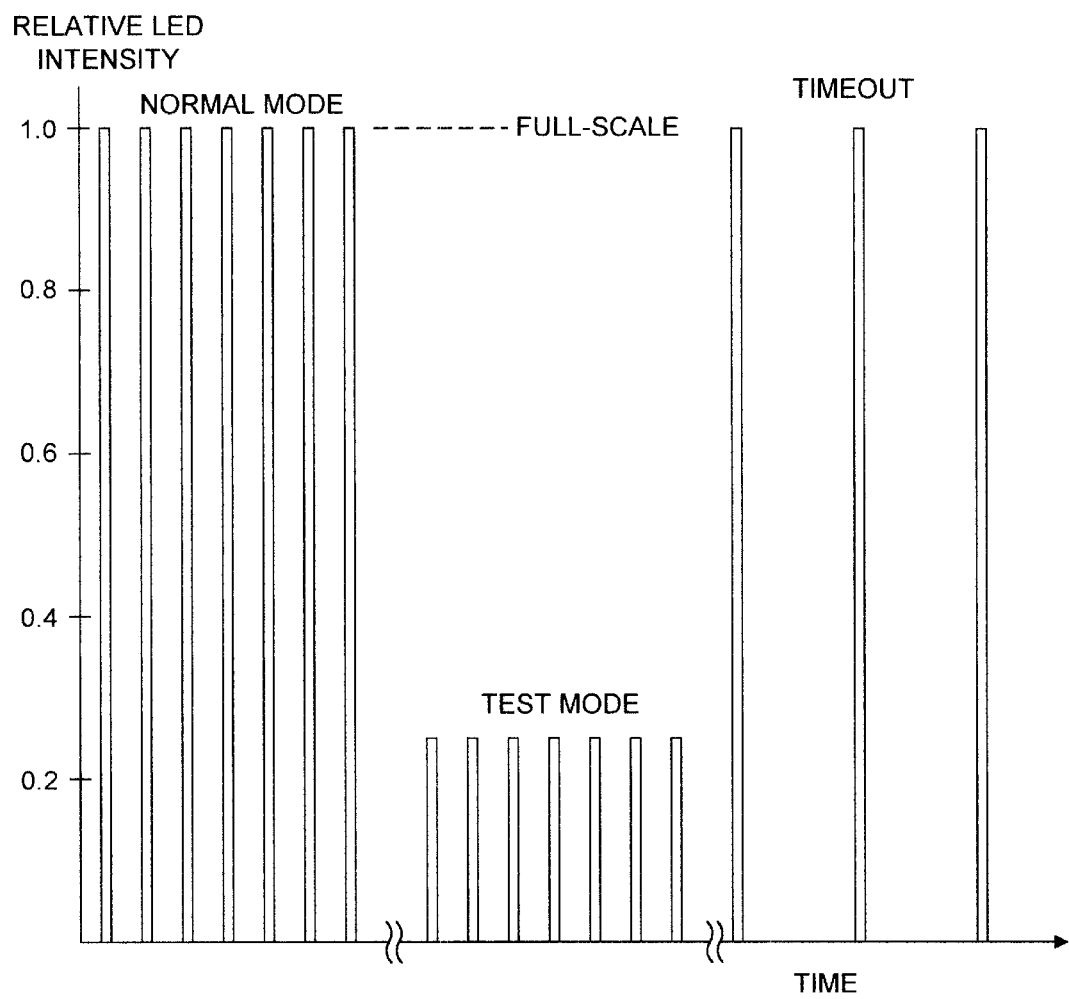
FIG. 5b is a graph of the emitter pulse intensity versus time for normal operation, test mode, and a reduced duty-cycle after timeout.

FIG. 5b shows an alternative method of reducing exposure after timeout. Here, the pulse intensity is the same as in normal operation, but the duty-cycle is reduced. With this method, density measurements continue to be obtained as in the normal mode, over the full density range, but at a lower sampling frequency, while the web motion is stopped. Calculation of an indirect or inferred motion signal, based on density measurement variability, is possible at all times, whether the belt is actually moving or not. When it is determined that motion has resumed, the duty-cycle is switched back to the normal duty-cycle. The duty-cycles shown are illustrative only; other duty-cycle values may be used according to the application. The normal duty-cycle may even be as high as 100%. That is, the LED may be energized continuously during normal operation while the web is moving, but pulsed with a reduced duty-cycle while the web motion is stopped.

CONCLUSION, RAMIFICATIONS, AND SCOPE

A densitometer with a light emitter intensity controlled in both intensity and duty-cycle has been disclosed. Presently preferred embodiments have been described illustrating several advantages. Pulsed-mode operation is used to reduce emitter temperature, reduce variability during warm-up, and prolong emitter useful life. Exposure of the photoconductor is reduced, which can prolong its useful life and avoid image defects. Emitter pulse width, frequency, and duty-cycle are chosen according to effective measurement spot size and photoconductor velocity in a way that does not seriously compromise density measurement capability. The density output is held steady between pulses, providing more readable display and simpler output to a computer. The emitter drive circuitry is connected to a photoconductor motion sensor. Exposure from the emitter is reduced to a low level when motion is stopped, thus avoiding harm to the photoconductor spot opposite the emitter. A test mode is provided during which the emitter intensity is reduced by a calibrated amount, simulating the insertion of a calibrated test standard. An emitter stabilization circuit regulates the emitter light output, even when there is no room to position a sensor to directly monitor the densitometer emitter light output.

While the preceding description is specific to the preferred embodiment, it will be recognized that other embodiments are possible. Densitometer light emitters other than LED's, for example, are within the spirit and scope of the invention. It will also be recognized that the present invention may be used in other applications besides electrophotographic copies and printers.

What is claimed is:

1. A pulsed-mode densitometer for determining the optical density of a test sample, said densitometer comprising:
   a light emitter operated in a pulsed-mode at a pulse frequency;
   a photodetector; and
   a converter to convert the output of said photodetector and provide a density output indicating the optical density of said test sample;
   wherein while said test sample is in motion said pulse frequency is in the range greater than 1.0 and at most 5.0 times the ratio of said test sample velocity to the effective measurement spot diameter on said test sample.

2. A pulsed-mode densitometer as set forth in claim 1, further including means to hold steady said output density between said light emitter pulses, whereby said density output is updated for each said light emitter pulse and holds steady between said light emitter pulses.

3. A pulsed-mode densitometer as set forth in claim 2, wherein said means to hold steady is a sample-and-hold circuit adapted to sample said photodetector output during said light emitter pulses, whereby said sample-and-hold output and said density output are held steady between said emitter pulses.

4. A pulsed-mode densitometer as set forth in claim 2, wherein said means to hold steady is a latching signal synchronous with said emitter pulses, input to an analog-to-digital converter, whereby said analog-to-digital converter output and said density output are held steady between said emitter pulses.

5. A pulsed-mode densitometer as set forth in claim 2, wherein said means to hold steady is a latching signal synchronous with said emitter pulses, input to a density lookup table memory, whereby said lookup table output and said density output are held steady between said emitter pulses.

6. A pulsed-mode densitometer as set forth in claim 1, wherein said light emitter duty-cycle is less than 50 percent.

7. A pulsed-mode densitometer as set forth in claim 1, further including a receiver to receive an encoder pulse signal synchronous with said motion, wherein said encoder pulse signal triggers each pulse of said light emitter, whereby said density output provides density measurements at a defined spacing on said test sample.

8. A densitometer for determining the optical density of a test sample, said densitometer comprising:
   a light emitter with a drive circuit adapted to energize said light emitter, with a selectable intensity selected from a predetermined full intensity and at least one predetermined reduced intensity;
   a photodetector; and
   a converter to convert the output of said photodetector to an output measurement of the density of said test sample;
   wherein said drive circuit is responsive to a motion signal indicating motion status of said test sample, said drive circuit switching said light emitter to a reduced intensity when said motion signal indicates that said test sample motion has stopped, thereby preventing excessive light exposure of a spot on said test sample, and said drive circuit switching said light emitter to said full intensity when said motion signal indicates that said test sample motion has resumed.

9. A densitometer as set forth in claim 8, further including an encoder producing said motion signal in the form of pulses synchronous with the motion of said test sample.

10. A densitometer as set forth in claim 8, wherein said motion signal is derived from variability in a sequence of density measurements, indicating motion when said variability exceeds a predetermined threshold over a predetermined time period.

11. A densitometer for determining the optical density of a test sample, said densitometer comprising:
   a light emitter with a drive circuit adapted to energize said light emitter in a pulsed-mode, with a selectable duty-cycle value selected from a predetermined normal duty-cycle and at least one predetermined reduced duty-cycle;
   a photodetector; and
   a converter to convert the output of said photodetector to an output measurement of the density of said test sample;
   wherein said drive circuit is responsive to a motion signal indicating motion status of said test sample, said drive circuit switching said light emitter to a reduced duty-cycle when said motion signal indicates that said test sample motion has stopped, thereby preventing excessive light exposure of a spot on said test sample, and said drive circuit switching said light emitter to said normal duty-cycle when said motion signal indicates that said test sample motion has resumed.

12. A densitometer as set forth in claim 11, further including an encoder producing said motion signal in the form of pulses synchronous with the motion of said test sample.

13. A densitometer as set forth in claim 11, wherein said motion signal is derived from variability in a sequence of density measurements, indicating motion when said variability exceeds a predetermined threshold over a predetermined time period.

14. A densitometer for determining the optical density of a test sample, said densitometer comprising:
   a light emitter with a drive circuit adapted to produce at least two selectable light intensities;
   a photodetector; and
   a converter to convert the output of said photodetector to an output measurement of the density of said test sample;
   wherein during a test mode of operation the intensity of said light emitter is reduced by a predetermined factor, simulating the insertion of a calibrated test standard of a corresponding density, whereby the function and accuracy of said densitometer can be tested.

15. A densitometer for determining the optical density of a test sample, said densitometer comprising:
   a first light emitter;
   a first photodetector disposed to detect light from said first light emitter;
   a converter to convert the output of said first photodetector and provide a density output indicating the optical density of said test sample when said test sample is positioned to block a portion of light from said first light emitter from impinging on said first photodetector;
   a second light emitter identical to said first light emitter, connected electrically such that at every instant the current in said first light emitter is equal to the current in said second light emitter;

a second photodetector disposed to monitor the light output from said second light emitter; and an emitter stabilization circuit responsive to said second photodetector output and adapted to adjust the current in said first and second light emitters according to the light output deviation of said second light emitter from a predetermined setpoint value, such that said second light emitter output is regulated to said setpoint value, whereby said first light emitter output is also approximately regulated to said setpoint value.

16. A densitometer as set forth in claim 11, wherein said predetermined normal duty-cycle is 100 per cent.

17. A densitometer as set forth in claim 14, wherein said predetermined factor is in the range from 1.41 to 10.0, thereby simulating a calibrated test standard of optical density in the range of 0.15 to 1.00.

18. A densitometer as set forth in claim 14, wherein during said test mode of operation the drive current in said light emitter is reduced by approximately said predetermined factor, such as to reduce the intensity of said light emitter by said predetermined factor, simulating the insertion of said calibrated test standard, whereby the function and accuracy of said densitometer can be tested.

19. A method for testing the function and accuracy of a densitometer having a light emitter with at least two selectable light intensities, said method comprising:

driving said light emitter at a first light intensity;

obtaining a first densitometer output corresponding to said first light intensity;

driving said light emitter at a second light intensity, said second light intensity being a predetermined fraction of said first light intensity, where said fraction corresponds to the optical density of a simulated optical filter;

obtaining a second densitometer output corresponding to said second light intensity;

determining a densitometer output difference between said second densitometer output and said first densitometer output; and comparing said densitometer output difference to a specification corresponding to said simulated optical filter.

20. A method for testing the function and accuracy of a densitometer as set forth in claim 19, wherein:

a first emitter drive current is employed to obtain said first light intensity; and a second emitter drive current is employed to obtain said second light intensity.

* * * * *